(12) United States Patent
Čurin-Šerbec

(10) Patent No.: US 7,098,317 B1
(45) Date of Patent: Aug. 29, 2006

(54) ANTIBODIES CAPABLE TO SELECTIVELY DETECT PRION PRP$^{SC}$ ISOFORMS

(75) Inventor: Vladka Čurin-Šerbec, Ljubljana (SI)

(73) Assignee: Blood Transfusion Center of Slovenia, Ljubljana (SI)

( * ) Notice: Subject to any disclaimer, the term of this patent is extended or adjusted under 35 U.S.C. 154(b) by 0 days.

(21) Appl. No.: 09/576,724

(22) Filed: May 23, 2000

(51) Int. Cl.
*C12P 21/08* (2006.01)

(52) U.S. Cl. .............................. 530/388.1; 424/139.1; 424/141.1

(58) Field of Classification Search ................ 424/9.1, 424/139.1, 141.1; 435/7.1, 70.1, 71.1; 436/501, 436/547; 520/388.1, 389.1
See application file for complete search history.

(56) References Cited

U.S. PATENT DOCUMENTS

| | | | | |
|---|---|---|---|---|
| 5,773,572 A | * | 6/1998 | Fishleigh et al. | 530/323 |
| 5,846,533 A | * | 12/1998 | Prusiner et al. | 424/130.1 |
| 6,261,790 B1 | * | 7/2001 | O'Rourke | 424/130.1 |
| 6,765,088 B1 | * | 7/2004 | Korth et al. | 530/388.1 |

FOREIGN PATENT DOCUMENTS

| | | |
|---|---|---|
| DE | 197 41 607 A1 | 3/1999 |
| GB | 0 861 900 A1 * | 2/1998 |
| WO | WO 93/11155 | 6/1993 |
| WO | WO 97/10505 | 3/1997 |

OTHER PUBLICATIONS

Korth et al. Prion (PrPSc)-specific epitope defined by monoclonal antibody. Nature (1997) vol. 390, pp. 74-78.*
Kocisko et al., "Partial Unfolding and Refolding of Scrapie-Associated Prion Protein: Evidence for a Critical 16-kDa C-Terminal Domain," *Biochemistry* 35:13434-13442 (1996).
Muramoto et al., "Recombinant Scrapie-Like Prion Protein of 106 Amino Acids is Soluble," *Proc. Natl. Acad. Sci. USA*, 93:15457-15462 (1996).
Rubenstein et al., "Immune Surveillance and Antigen Conformation Determines Humoral Immune Response to the Prion Protein Immunogen," *Journal of Neurovirology* 5:401-413 (1999).
Čurin-Šerbec, "Site-Directed Monoclonal Antibody Specifically Recognizes PrP$^{Sc}$," *Vox Sanguinis—26$^{th}$ Congress of the International Society of Blood Transfusions*, Viena, Austria 78(1):57 (2000) (abstract).

* cited by examiner

*Primary Examiner*—Ulrike Winkler
(74) *Attorney, Agent, or Firm*—Nixon Peabody LLP

(57) ABSTRACT

The present invention pertains to novel antibodies directed to the C-terminal part of the PrP$^{Sc}$ isoform of prions. In particular, the present invention pertains to the use of such antibodies in the diagnosis of bovine spongiform encephalopathy (BSE) and the new variant form of Creutzfeld Jacobs Disease (vCJD). In addition, the present invention relates to the peptide recognized by the antibodies and its use in the immunization and/or treatment of BSE, CJD, vCJD and other TSE related diseases.

2 Claims, 7 Drawing Sheets

ANTIBODIES CAPABLE TO SELECTIVELY DETECT PRION PRP$^{SC}$ ISOFORMS

The present invention pertains to novel antibodies directed to the C-terminal part of the PrP$^{Sc}$ isoform of prions. In particular, the present invention pertains to the use of such antibodies in the diagnosis of bovine spongiform encephalopathy (BSE), the new variant form of Creutzfeld Jacobs Disease (vCJD), sporadic CJD and scrapie.

Starting in 1986 a chronic degenerative disease has been diagnosed in the United Kingdom. Cattle affected by this disease experienced progressive degeneration of the nervous system, displayed changes in temperament, such as nervousness or aggression, abnormal posture, incoordination and difficulty in rising, decreased milk production, or loss of body weight despite continued appetite. The affected cattle eventually died.

This disease had been termed Bovine Spongiform Encephalopathy (BSE) and is now widely referred to as "mad cow disease". During the following ten years approximately 160 000 cases of this newly-recognized cattle disease were confirmed in the United Kingdom, while also in other European countries and even in countries abroad, e.g. Canada, The Falkland islands and the Oman Sultanate animals suffering from said disease were reported.

BSE is associated with a transmissible agent, the nature of which is not yet fully understood. The agent affects the brain and spinal cord of cattle and lesions are characterized by sponge-like changes visible by means of a microscope. This agent is highly stable, and withstands heating to normal cooking temperatures and to even higher temperatures such as those used for pasteurization, sterilization at usual temperatures and time periods, as well as to freezing and drying.

In cattle naturally infected with BSE, the BSE agent has been found only in brain tissue, in the spinal cord, and in the retina. Additional studies have identified BSE infectivity in the distal ileum, bone marrow, dorsal root ganglion, and trigeminal ganglion of calves that had been fed brain material from BSE-infected animals.

In human beings a similar degenerative syndrome is known, which is termed Creutzfeld-Jacobs disease (CJD). CJD is a slow degenerative human disease of the central nervous system with obvious dysfunction, progressive dementia, and vacuolar degeneration of the brain. CJD occurs sporadically worldwide at a rate of 1 case per 1 million people per year. More rare are the related TSE (Transmissible Spongiform Encephalopathy) conditions of the Gerstmann-Straussler syndrome, kuru and fatal familial insomnia.

In 1996, the UK's Spongiform Encephalopathy Advisory Committee (SEAC) announced the identification of 10 cases of a new variant form of CJD (vCJD). All of the patients developed onset of illness in 1994 or 1995. However, the 10 cases reported vastly differed from the sporadic form of CJD. The affected individuals were much younger than the classical CJD patient. Typically, CJD patients are over 63 years old. In contrast thereto, the average patient's age for the onset of variant CJD was about 28. The course of the disease in the vCJD averaged 13 months which differs from classical CJD cases, which average a 6 month duration. In the variant cases, electroencephalographic (EEG) electrical activity in the brain was not typical of sporadic CJD. Although brain pathology was recognizable as CJD, the pattern was different from sporadic CJD, with large aggregates of prion protein plaques.

According to the SEAC, all victims were reported to have eaten beef or beef products in the last 10 years, indicating a causative relationship between vCJD and BSE. Two studies published in 1997 confirmed the assumption that the BSE agent is highly likely to be the cause of vCJD. To this end, a group of researcher infected three panels of inbred mice and one panel of crossbred mice with BSE, vCJD and sporadic CJD, respectively. Interim results indicated that mice inoculated with BSE showed the same pattern of incubation time, clinical signs and brain lesions as mice inoculated with tissues from patients with vCJD from which it was concluded that BSE and vCJD have the same signature or are the same "strain". Furthermore, sporadic CJD and known scrapie strains were not similar to vCJD or BSE. These results have been confirmed by other researchers so that it is presently believed that BSE may be transmitted to human beings resulting in the development of vCJD.

Due to the increasing public and scientific concern about the possibility of BSE being transmitted to the human population as a result of consumption of products derived from infected cattle it has been suggested that cattle suffering from BSE should be slaughtered and their carcasses should not be introduced into the human food chain. However, given that BSE takes typically five or more years to become manifest as the result of the behaviour of an infected animal and due to the fact that there has been no quick method of assessing the probability of whether or not a particular cow is suffering from BSE other than examining the brain of the slaughtered animal, it has been suggested that the only safe approach to adopt, which will in addition calm public fears about the safety of eating beef products, is widespread slaughter. It is almost inevitable that such a policy will result in the slaughter of many thousands of cattle which are not infected with BSE. Consequently, there is a need in the art for a quick determination method of BSE.

One method presently available to determine the presence of the BSE agent in tissues is to inoculate animals, usually mice, with material believed to be infected with BSE. Mouse inoculation studies take, however, a long time of up to 700 days, and failure to identify it in tissues may indicate either true absence of the agent or simply the limited sensitivity of this approach.

The agent responsible for the development of BSE and other TSE's, such as the vCJD, is smaller than the smallest known virus and has not been completely characterized yet. There are three main theories on the nature of the agent. (1) The agent is a virus with unusual characteristics, (2) the agent is an exclusively host-coded protein ("prion") that is modified to a partially protease-resistant form after infection, and (3) the agent is a small, non-coding regulatory nucleic acid coated with a host-derived protective protein. The BSE agent is extremely resistant to heat and to normal sterilization processes. It also does not evoke any detectable immune response or inflammatory reaction in host animals.

In the recent past it has now been found that the agent responsible for the disease is distinct from viruses. The agent can exist in multiple molecular forms, whereas viruses exist in a single form with distinct ultrastructural morphology. Second, these agents are non-immunogenic, in contrast to viruses, which almost always provoke an immune response. Third, there is no evidence for an essential nucleic acid within the infectious particle, whereas viruses have a nucleic acid genome which serves as the template for the synthesis of progeny virus. Thus, it was eventually concluded that prions are the cause for the degenerative disease, the only known component thereof is the prion, which is encoded by a chromosomal gene of the individual itself.

Infectious prions are essentially composed of a protein designated as the "scarpie isoform" of the prion protein, abbreviated as PrP$^{Sc}$. A post-translational process, as yet undefined, obviously generates PrP$^{Sc}$ from the ubiquitous cellular prion protein PrP$^C$. Both, PrP$^{Sc}$ and PrP$^C$ are encoded by a single copy chromosomal gene and it has been shown that the inoculated prion initiates the production of PrP$^{Sc}$ from the normal host PrP$^C$ polypeptide. In contrast to the normal form, which is mainly found on the cell surface the isoforms are accumulated within the cells in vesicles. The isoforms also differ in their conformational structure, exhibited by an increased β-sheet content which might be a cause for the increased protease resistance of the PrP$^{Sc}$ isoform versus the normal form PrP$^C$.

At present there is no treatment nor any vaccine available to prevent the disease. This may be mainly due to the obvious low immunogeneicity of the PrP$^{Sc}$ isoform which has prevented the manufacture of antibodies specifically recognizing the PrP$^{Sc}$ isoform, while simultaneously avoiding cross-reactivity with the "normal" isoform, PrP$^C$.

Moreover, there is also no adequate test to detect the disease in a live animal. Veterinary pathologists may confirm BSE by postmortem microscopic examination of brain tissue. Yet, when it comes to detect the presence of the BSE agent in tissues this is determined by inoculating animals, usually mice, with material believed to be infected with BSE. Thus, there exists a need in the art to provide a means with which the agents responsible for the development of degenerative diseases of the nervous system, such as BSE, CJD, vCJD or TSE related diseases, like scrapie and others.

The problem of the present invention therefore resides in providing means, which enables a veterinary and/or physician to specifically detect the presence of agents causing BSE, CJD, vCJD and/or TSE related diseases.

FIG. 7 shows the results of a Dot Blot experiment, wherein various samples of normal brain tissues are exposed to the antibody CNCM-I-2476. As a control the peptide of SEQ. ID. No. 1 and the conjugate of said peptide and KLH was used.

Thus, according to an embodiment the present invention provides for an antibody directed to the C-terminal part of the PrP$^{Sc}$ isoform or a part thereof, that is, to a three dimensional conformation of said part of the prion polypeptide exhibited in the "misfolded" form. Since the PrP$^C$ form does exhibit a three dimensional conformation in this part of the prion polypeptide obviously different from PrP$^{Sc}$ the present antibodies are capable to selectively bind to the PrP$^{Sc}$ isoform while not binding to the PrP$^C$ form. They are therefore capable to distinguish between those isoforms. The antibodies are preferably directed to the region comprised by amino acids no. 190 to 214 of PrP$^{Sc}$ or a part thereof, more preferably to the sequence from about 202 to about 214 of PrP$^{Sc}$, or a part thereof, or to variants obtained by substituting or omitting one or more amino acids with the proviso that the conformational particularity of said region as exhibited by the PrP$^{Sc}$ isoform is essentially retained. According to a preferred embodiment the amino acid sequence is (SEQ. ID. No. 1) -Cys-Ile-Thr-Gln-Tyr-Glu-Arg-Glu-Ser-Gln-Ala-Tyr-Tyror (SEQ. ID. No. 2) -Cys-Ile-Thr-Gln-Tyr-Gln-Arg-Glu-Ser-Gln-Ala-Tyr-Tyr- The following sequence (SEQ. ID. No. 3) shows a part of the C-terminal region of the amino acid sequence of the bovine prion polypeptide that is from amino acid no. 180 to no. 219 as identified in the present invention.

```
Thr-Thr-Lys-Gly-Glu-Asn-Phe-Thr-Glu-Thr-Asp-Ile-Lys-Met-Met-Glu-
180                 185                 190                 195

Arg-Val-Val-Glu-Gln-Met-Cys-Ile-Thr-Gln-Tyr-Gln-Arg-Glu-Ser-Gln-
                200                 205                 210

Ala-Tyr-Tyr-Gln-Arg-Gly-Ala-Ser
            215
```

In the course of the extensive studies leading to the invention the present inventors have found that one of the conformational changes, the PrP$^C$ undergoes in its transformation to PrP$^{Sc}$ resides in a modification of the tertiary structure of the C-terminal region of PrP$^C$.

In the figures.

Figure 1:
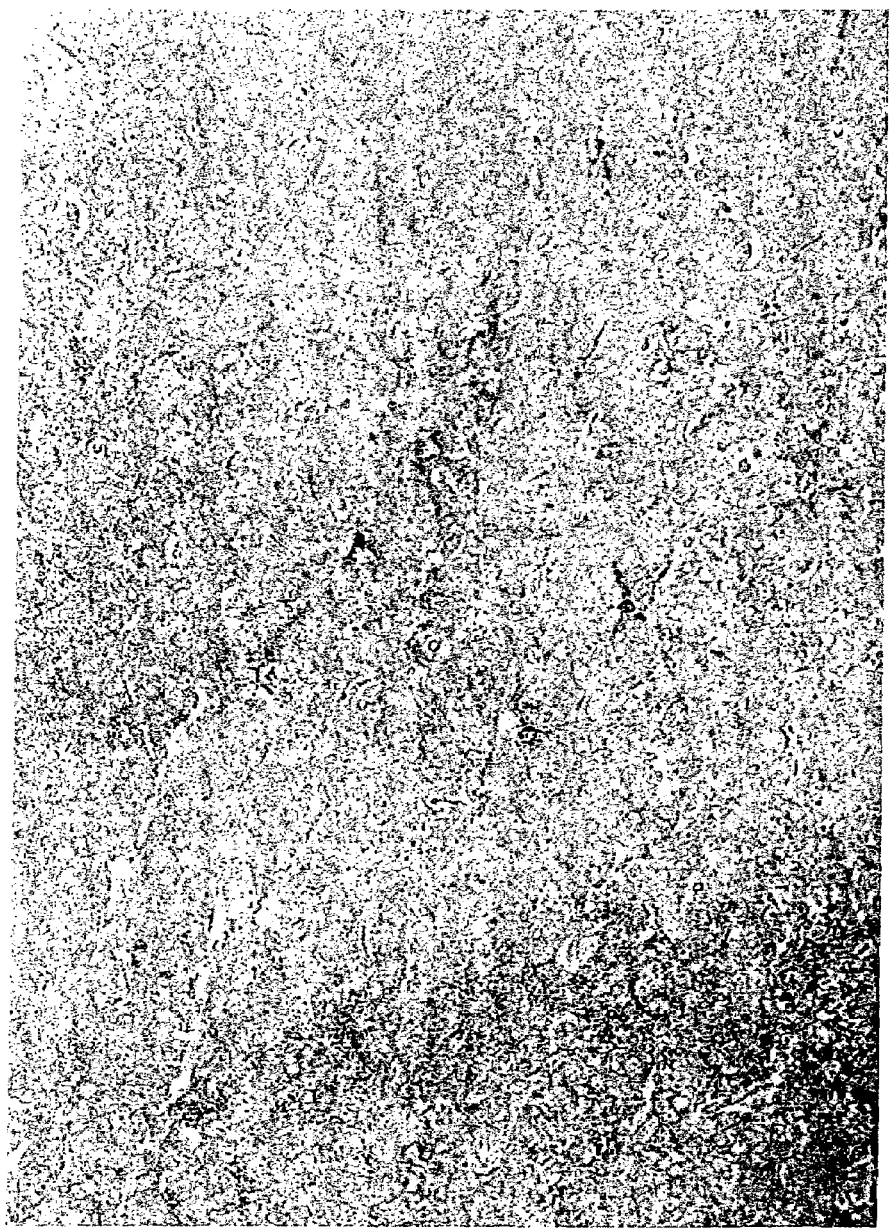
FIG. 1 shows a picture (10 tines enlarged) of a human brain tissue sample derived from an individuum subject to sporadic CJD treated with the antibody CNCM I-2476.

An antibody as defined here in the present invention shall be capable to differentiate between PrP$^{Sc}$ and PrP$^C$ by selectively binding to a three dimensional conformation provided by the C-terminal part of the PrP$^{Sc}$ isoform, which is not present in the PrP$^C$ form.

The antibody may be polyclonal or monoclonal, while due to cross-reactivity reasons monoclonal antibodies are preferred. Moreover, also fragments of the antibodies are within the meaning of the present antibodies, in particular those fragment binding to the target, such as the F$_{ab}$ regions or parts thereof. Based on the respective need the skilled person will be able to design the corresponding fragments.

The term antibodies is meant to also comprise chimeric antibodies, such as humanized antibodies, wherein the constant region is derived from a human source, while the variable region is derived from animal source, such as mice, so as to decrease a response of the treated individual to the agent. Bispecific antibodies are considered in the present invention as well. Bispecific antibodies are immunoglobulins or fragments thereof wherein the two F$_{ab}$ fragments are directed to different targets each. Thus, one F$_{ab}$ fragment will be directed to the C-terminal part of PrP$^{Sc}$ while the other F$_{ab}$ fragment may be directed to any target, such as a target to used in an assay.

The antibody may be linked to markers commonly used in the detection of targets, such as a radioactive label, a fluorescent label or a dye. According a preferred embodiment the antibody is the antibody produced by the hybridoma cell line CNCM I-2476, deposited according to the Budapest Treaty with the Pasteur Institute, Paris, France on May 10$^{th}$, 2000.

The above antibodies may be used for the diagnosis and/or treatment of Bovine Spongiform Encephalopathy or Creutzfeld-Jacobs-Disease or variant form thereof or TSE related diseases in mammals, such as e.g. ungulates or humans, in that the antibody selectively binds to the PrP$^{Sc}$ isoform. This trait of being capable to use the present antibodies in different species, e.g. human, cow, sheep etc. is a novel and intriguing feature of the present antibodies and alleviates the determination methods, such that only one antibody is requierd to investigate all respective individuals.

For determining whether an individual is affected by the corresponding disease a specimen is taken from the individual to be tested, such as a tissue (homogenisate or sections) or a body fluid, e.g. blood, saliva urine or cerebrospinal fluid, and is examined for the presence of the PrP$^{Sc}$ isoform, by contacting the specimen under suitable conditions with the antibody.

The method for contacting the specimen with the antibody is not subject to any particular restriction and will be dependent only on the means available and the specimen itself. Hence, the antibodies may be used e.g. in the methods of ELISA, Dot Blot, Western Blot, immunohistochemistry methods and others, all of which the skilled person is well aquainted with.

In order to enable a rapid testing of an individual for the presence of a prion associated disease the present invention also provides for a kit, which comprises at least one antibody according to the present invention. In addition, the kit will also comprise buffers, support material and marker agents adapted to the respective assays performed.

Further, the antibodies of the present invention may also be used in the therapy of prion associated diseases by administering to an affected individual an effective amount of an antibody of the present invention, optionally together with suitable excipients and carriers. Consequently, the present invention will also comprise a pharmaceutical composition containing at least one antibody according to the present invention.

Moreover, the present invention also provides for a method for immunizing an individual against the PrP$^{Sc}$ isoform. In this respect peptides of the C-terminal part found to be different from the normal form (PrP$^{C}$) may be used for eliciting an immune response in an individudual, which peptides are preferably derived from the prion sequence amino acid no. 190 to 215 or a part thereof, more preferably from the sequence from about 202 to about 214 of the polypeptide, or a part thereof, or from variants obtained by substituting or omitting one or more amino acids with the proviso that the conformational particularity of said region as exhibited by the PrP$^{Sc}$ isoform is essentially retained. According to most preferred embodiment the amino acid sequence is (SEQ. ID. No. 1) -Cys-Ile-Thr-Gln-Tyr-Glu-Arg-Glu-Ser-Gln-Ala-Tyr-Tyror (SEQ. ID. No. 2) -Cys-Ile-Thr-Gln-Tyr-Gln-Arg-Glu-Ser-Gln-Ala-Tyr-Tyr- In addition the antibodies itself may be used to produce antiidiotypic antibodies, which may be used for immunization. It will be appreciated that for the immunization the skilled person will choose the appropriate time frame between the boosting steps and will select an proper adjuvant if deemed necessary.

The present antibodies may also be used for raising anti-idiotype antibodies, i.e. antibodies that are directed to the binding region of the antibodies of the present invention. These anti-idiotypic antibodies represent a mirror-image of the antibodies of the present invention and may be used for the prevention and therapy of the above mentioned diseases. The anti-idiotypic antibodies are therefore also within the scope of the present invention and may be produced according to methods well known in the art, i.e. by immunizing animals with e.g. the hypervariable region of the antibodies of the present invention and producing polyclonal or monoclonal antibodies against it. In a next step the antibodies obtained will be selected according to the binding of the present antibodies to said anti-idiotypic antibodies.

The method for obtaining the antibodies of the present invention comprises the step of immunizing an animal, such as e.g. mice or rabbit with an immunizing amount of a peptide comprising the amino acids of the C-terminal part of the prion polypeptide, preferably a peptide having the following a sequence:

(SEQ. ID. No. 2) -Cys-Ile-Thr-Gln-Tyr-Gln-Arg-Glu-Ser-Gln-Ala-Tyr-Tyr-

More preferably, for the immunization step a peptide is used that had been derived from the above sequence by replacing the Gln residue at location no. 207 of the prion polypeptide by Glu to obtain the following amino acid sequence:

(SEQ. ID. No. 1) -Cys-Ile-Thr-Gln-Tyr-Glu-Arg-Glu-Ser-Gln-Ala-Tyr-Tyr-

This sequence has surprisingly proven to elicit an immune response sufficiently strong to be capable to easily raise antibodies specifically against PrP$^{Sc}$. Without being bound to any theory the surprising result obtained with this peptide may reside in that the native Gln residue may form hydrogen bonds and may such cause insolubility of the peptide, which is not desired when being part of an epitope. On the other hand Glu, which is in the sequence of the human PrP, whereas Gln is at the same position in the primary structure of bovine PrP, seemingly does not form such links.

Using any of the above peptides for the immunization step harbors the advantage that no knock out mice have to be prepared in before, such as when using the entire prion polypeptide. For the immunization preferably a conjugate of the peptide and a carrier is used, wherein the peptide is bound to the carrier via its N-terminus. It could be shown that this measure obviously provides for a better immune response as compared to binding the peptide to the carrier via the C-terminus.

After immunizing animals with the antigen spleenocytes are isolated and fused with myeloma cells according to methods and techniques well known in the art. Selection for fused cells is performed using an appropriate medium, which does not support growth of unfused cells, such as the HAT medium. Fused myeloma cells growing in the selection medium are screened for the production of antibodies capable to bind to the peptide used for the immunization step.

The present invention also pertains to hybridoma cell lines capable of producing the antibodies of the present invention and obtainable according to the above method. The lines obtained were found to grow extremely fast, with a doubling time period of about 8 hours. Also the secretion of antibodies was found to be very high as compared to normal hybridoma antibody secretion. According to a preferred embodiment the hybridoma is CNCM I-2476 which has been deposited with the Institute Pasteur, Paris, France on May 10$^{th}$, 2000 according to the Budapest Treaty.

According to another embodiment the present invention relates to a peptide sequence as shown by the following amino acid sequences:

(SEQ. ID. No. 2) Cys-Ile-Thr-Gln-Tyr-Gln-Arg-Glu-Ser-Gln-Ala-Tyr-Tyr or (SEQ. ID. No. 1) Cys-Ile-Thr-Gln-Tyr-Glu-Arg-Glu-Ser-Gln-Ala-Tyr-Tyr or peptides derived from these sequences by substituting or omitting one or more amino acids with the proviso that the three conformational structure is essentially maintained.

These peptides obviously provide for a three dimensional conformation exhibited exclusively by the PrP$^{Sc}$ isoform and not from the PrP$^{C}$ form. Thus, as mentioned above this peptide may well be used for immunizing humans or animals, so that the immunized individual may produce an immune response against the "misfolded form" of the prion polypeptide and depleting it from the body in a natural way. In addition, said polypeptide may also be used for producing drugs against the above mentioned prion associated diseases.

The following examples illustrate the invention without limiting it to the same.

EXAMPLE 1

Preparation of a Synthetic Peptide

For the immunization a 13-amino acid long peptide from the primary structure of the human PrP (human prion protein) has been chosen. The peptide is located close to the C-terminal part of the prion protein from amino acid 202 to 214. The peptide has been modified by exchanging the Gln residue at location 207 by a Glu residue to result in the following amino acid sequence (SEQ. ID. No. 1) H-Cys-Ile-Thr-Gln-Tyr-Glu-Arg-Glu-Ser-Gln-Ala-Tyr-Tyr-OH This peptide was bound via its N-terminal part to the carrier protein KLH, keyhole limpet hemocyanin, which represents a novel feature of linking potentially immunogenic peptides to a carrier, since normally the peptide is linked via the C-terminus to the carrier.

EXAMPLE 2

Immunization of Animals

BALB/c mice were immunized with 0.2 mg KLH-peptide conjugate (prepared according to example 1) per mouse, subcutaneously in Freund's complete adjuvant (CFA) (200 µl/mouse). After 14 days mice were again immunized with 0.1 mg of KLH-peptide per mouse in Freund's incomplete adjuvant (IFA), intraperitoneally (200 µl/mouse). After two weeks they were inoculated intraperitoneally with 0.2 mg of KLH-peptide per mouse intraperitoneally in Freund's incomplete adjuvant once more. Blood was taken from the tail vein 10 days after the last inoculation and the presence of antibodies against the conjugate was determined by indirect ELISA. Plates were coated with KLH, KLH-peptide and free peptide. The binding of mouse antibodies was detected by goat anti-mouse antibodies, conjugated with HRP. The immune response of all mice was surprisingly very high.

A final boost was injected intravenously in physiological solution (0.1 mg/mouse in 100 µl).

EXAMPLE 3

Production of Hybridomas

On day 4 after the booster injection mice were sacrificed and their spleen was removed. Splenocytes were isolated and fused with mouse myeloma cells NS1 (in ratio 10:4) using 50% PEG for 3 minutes according to standard techniques (Liddel, J. E., Cryer, A., A practical guide to monoclonal antibodies. John Wiley & Sons, New York, 1991). Cells were washed and resuspended into 96-well microtiter plates in DMEM (Flow, UK), supplemented with 13% FCS (HyClone, USA) (in the following merely designated DMEM) and with feeder layer of mouse thymocytes. The next day HAT DMEM was added into all wells. Supernatants were tested for the presence of specific antibodies after 10–14 days by indirect ELISA. To this end, microtiter plates (Nunc, Denmark) were coated with 5 µg/ml of the peptide or the KLH-peptide conjugate or KLH alone (Bachem, Switzerland) in 50 mM carbonate/bicarbonate buffer pH 9.6 overnight at +4° C. Plates were washed three times with PBS/Tween 20 (Sigma, USA) and blocked for 30 minutes with 1% BSA (Sigma, USA). After washing with PBS/Tween20 supernatants were added into the wells and incubated for 2 hours at 37° C. Plates were washed three times with PBS/Tween20 and goat anti-mouse immunoglobulins, conjugated with HRP (Sigma, USA) were added into the wells at dilution 1:5000 in 1% BSA. After two hours incubation at 37° C. plates were washed with PBS/Tween 20 and substrate was added to the wells (ABTS/H2O2; Sigma, USA). Plates were read at 410 nm. All volumes were 50 µl.

Hybridomas from positive wells were transferred into larger volumes (24-well plates) in HT DMEM medium. The presence of specific antibodies was determined by indirect ELISA again and selected lines were transferred into tissue culture flasks in DMEM. Finally, selected hybridomas were cloned twice by the limiting dilution method and frozen in liquid nitrogen.

The lines selected were growing extremely fast in DMEM, i.e. without the need of HT, with a doubling time period of about 8 hours. Also the secretion of antibodies was found to be very high. One of the clones obtained was submitted to the Pasteur Institute and received the deposit no CNCM I-2476.

EXAMPLE 4

Testing of the Antibodies

The reactivity of the monoclonal antibodies with PrP was tested using the supernatants of the stored clones. The monoclonal antibodies were tested by immuno-histochemistry on brain tissue from CJD patients, vCJD patients and on brains of BSE positive cattle and scrapie infected brains of sheep. For control normal human, bovine and sheep brains were used. The screening was also done by Western blot and dot blot.

Figure 2:
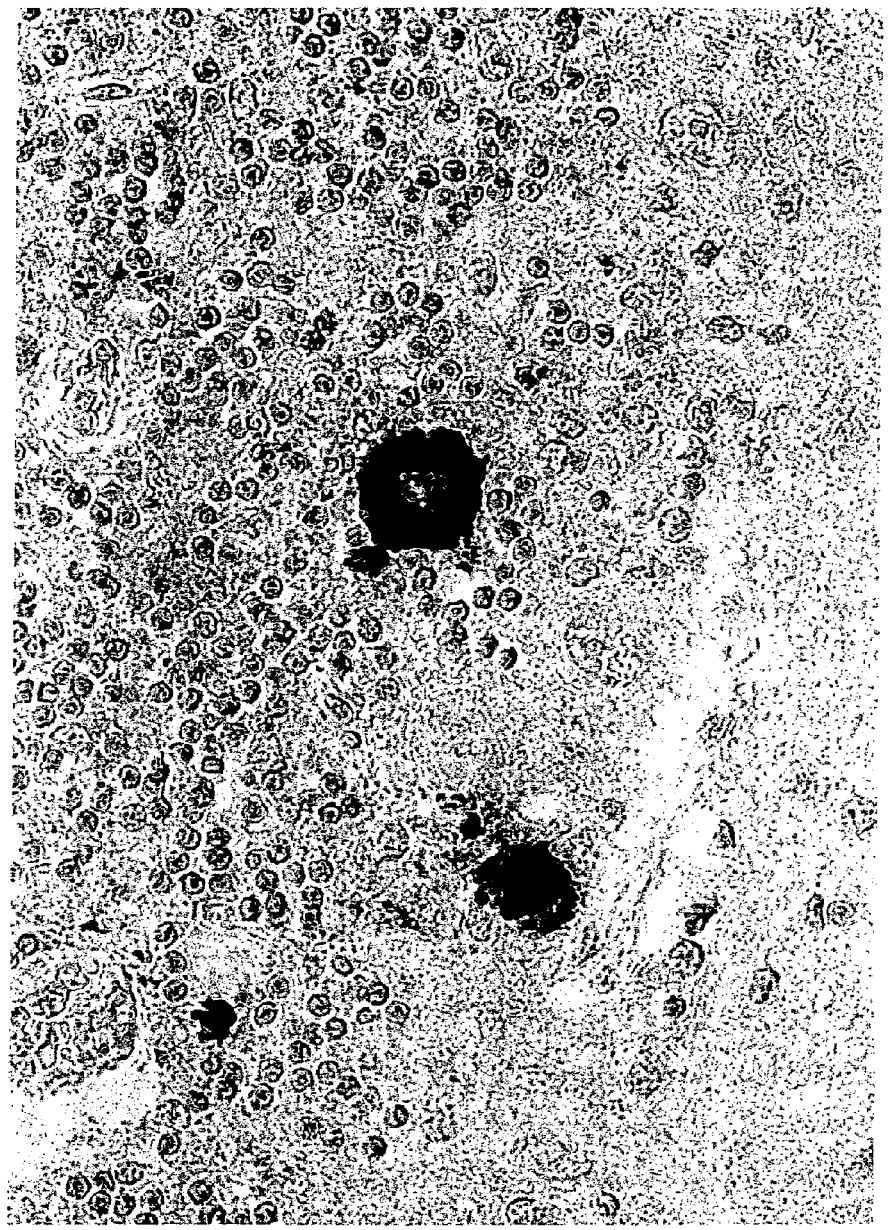
FIG. 2 shows a picture (60 times enlarged) of a human brain tissue sample derived from an individuum subject to sporadic CJD treated with the antibody CNCM I-2476.
Figure 3:
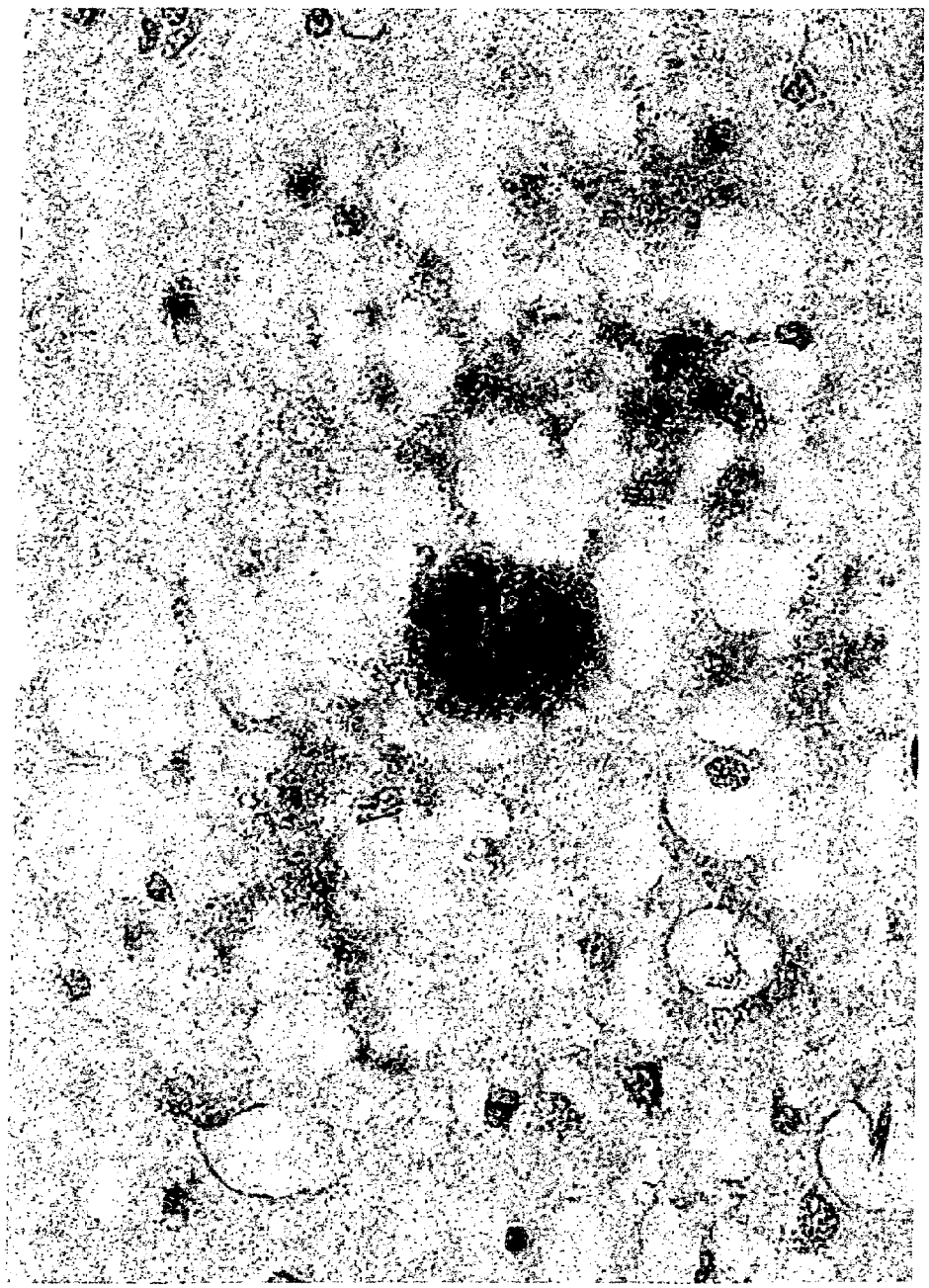
FIG. 3 shows a picture (60 times enlarged) of a human brain tissue sample derived from an individuum subject to new variant CJD treated with the antibody CNCM I-2476.
Figure 4:
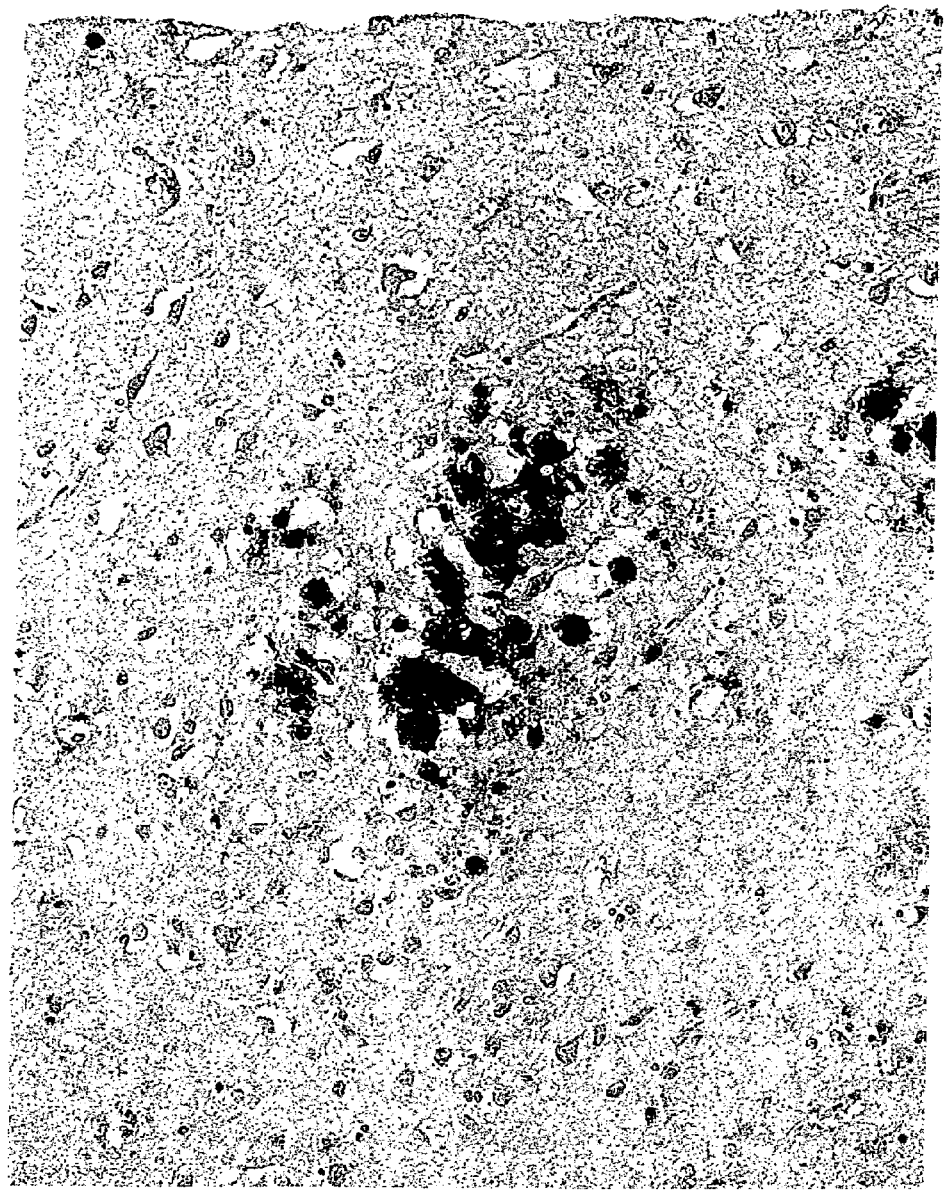
FIG. 4 shows a picture (20 times enlarged) of a human brain tissue sample derived from an individuum subject to new variant CJD treated with the antibody CNCM I-2476.
Figure 5:
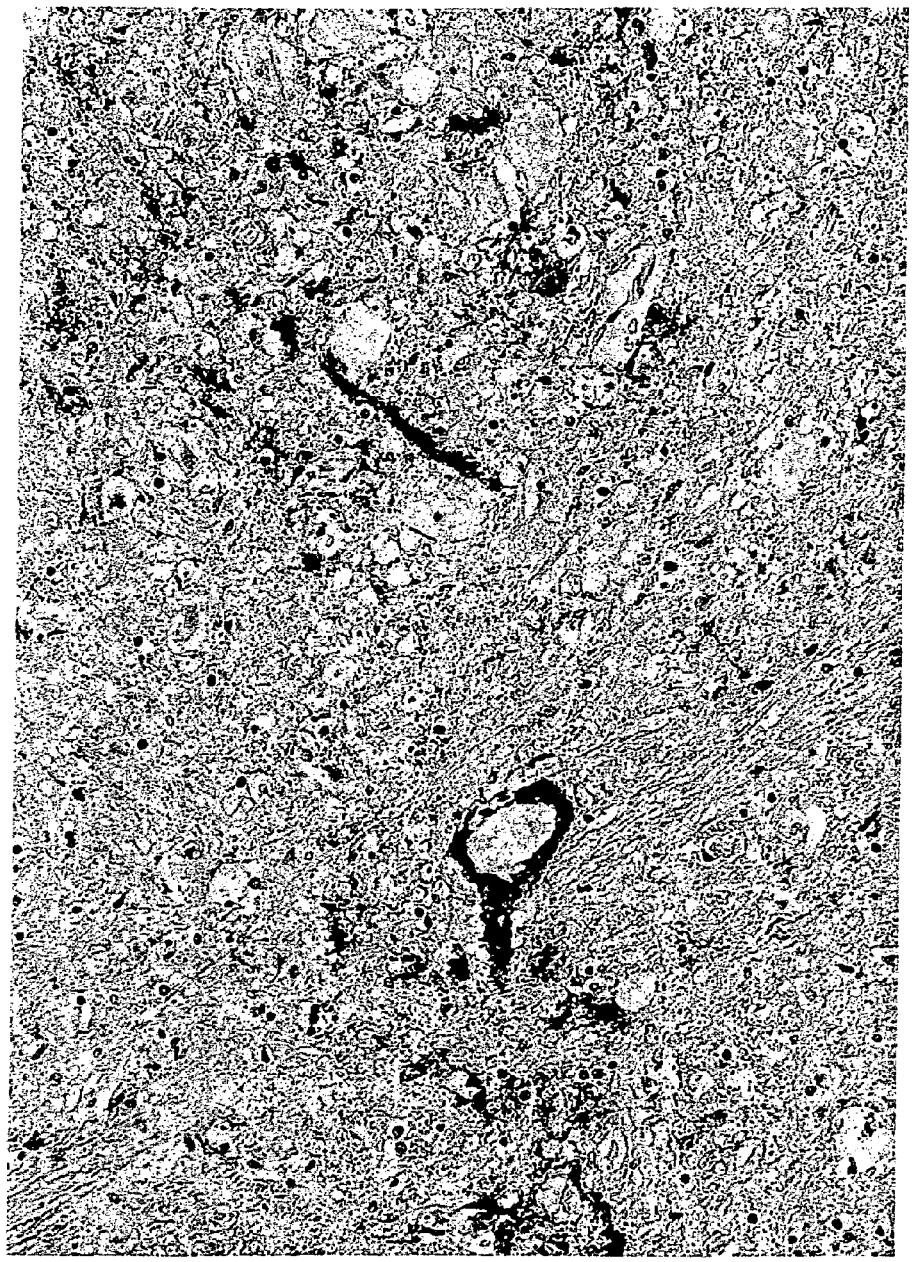
FIG. 5 shows a picture (20 times enlarged) of a bovine brain tissue sample derived from an animal exhibiting signs of BSE treated with the antibody CNCM I-2476.
Figure 6:
FIG. 6 shows a picture (10 times enlarged) of a brain tissue sample derived from a goat subject to scrapie treated with the antibody CNCM I-2476.
Figure 7:
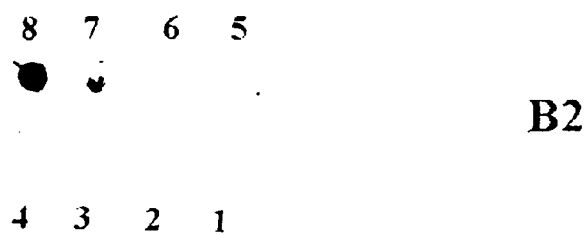

Sample Preparation for Histochemistry:

Paraffin sections of brain tissues derived from different sources (human, bovine and goat) were prepared according to standard techniques (machine: Ventana), wherein sections within 6–8 µm thickness were obtained. The samples were treated with HCOOH (FIG. 1, 5, 6) or not pretreated at all (FIG. 2–4). Subsequently endogenous peroxidase was blocked using a kit provided by (Ventana, USA), the antibodies were applied at a concentration of 4 µg/ml, diluted in Dako S-2022 (Dako, USA) and incubated for 20 minutes at 42° C.

Subsequently a biotinylated goat anti-mouse+rabbit was applied (Ventana, USA) and incubated for 20 minutes at 42° C., followed by an incubation with streptavidin HRP (Ventana) for 20 minutes at 42° C., DAB (diamino benzidine) with Cu for 4 minutes.

Results:

The pattern of the immunohistochemical reactions show that mAb CNCM I-2476 reacts with all known TSE forms from different species (human, bovine, sheep) and is reacting only with the pathological protein. There is no reaction on the brain tissue of healthy individuals and patients with Alzheimer disease.

Preparation of Brain Homogenates:

Brain tissue (thalamus or medulla or spinal cord) was homogenized in 10% sucrose, 20 mM HEPES pH 7.5, 2% sarcosyl and 5 mM EDTA with homogenizer (Potter) (5-times, 0.1 g in 1 ml). Homogenates were centrifuged for 45 minutes at +4° C. and 14 000 rpm. The supernatant was frozen at −20° C., whereas the pellet was dissolved in 1 M NaOH. The protein concentration in samples was determined by measuring absorbance at 280 and 260 nm.

Dot Blot:

10-times diluted supernatants or pellets were used as samples. They were used either native or digested with proteinase K (10 µg/ml and 100 µg/ml). Electrophoresis was done in Bio Rad cell with 25 mM Tris, 0.32 M glycin, 0.16% SDS (w/v) pH 8.3. The transfer was performed with 25 mM Tris, 192 mM glycine, 20% methanol (v/v), pH 8.3 on 0.2 mm PVDF membrane. Transfer was effected during 50 minutes at 100 V. The membranes were then blocked with 5% milk and incubated with monoclonal antibodies (for CNCM I-2476 40 µg/ml) in 1% milk for 1–2 hours (gentle shaking). After washing of the membranes they were incubated with secondary antibodies, conjugated with HRP (goat anti-mouse, Sigma, USA), diluted 1:5000 in 1% milk (1–2 hours, gentle shaking). Membranes were washed and immune reaction was detected using chemiluminescence kit (ECL, Amersham, USA).

Results:

No reaction of normal brain samples with antibody V5B2 (CNCM I-2476) occurred. As positive controls the KLH-peptide was used.

The monoclonal antibodies provided by the present invention show a high specificity for $PrP^{Sc}$. For recognition it was not required to use proteinase K digestion of $PrP^{C}$ prior to the screening method. There was no reaction between the normal brain tissues and the mAb under the same conditions, indicating that the produced antibodies are very specific and recognize exclusively $PrP^{Sc}$.

The invention claimed is:
1. A hybridoma cell line identified as CNCM I-2476.
2. A monoclonal antibody derived from a hybridoma cell line identified as CNCM I-2476, or a fragment thereof.

* * * * *

```
                        SEQUENCE LISTING

<160> NUMBER OF SEQ ID NOS: 3

<210> SEQ ID NO 1
<211> LENGTH: 13
<212> TYPE: PRT
<213> ORGANISM: Bos taurus

<400> SEQUENCE: 1

Cys Ile Thr Gln Tyr Glu Arg Glu Ser Gln Ala Tyr Tyr
 1               5                   10

<210> SEQ ID NO 2
<211> LENGTH: 13
<212> TYPE: PRT
<213> ORGANISM: Bos taurus

<400> SEQUENCE: 2

Cys Ile Thr Gln Tyr Gln Arg Glu Ser Gln Ala Tyr Tyr
 1               5                   10

<210> SEQ ID NO 3
<211> LENGTH: 40
<212> TYPE: PRT
<213> ORGANISM: Bos taurus

<400> SEQUENCE: 3

Thr Thr Lys Gly Glu Asn Phe Thr Glu Thr Asp Ile Lys Met Met Glu
 1               5                   10                  15

Arg Val Val Glu Gln Met Cys Ile Thr Gln Tyr Gln Arg Glu Ser Gln
            20                  25                  30

Ala Tyr Tyr Gln Arg Gly Ala Ser
        35                  40
```